US012642757B2

(12) United States Patent
Hu et al.

(10) Patent No.: US 12,642,757 B2
(45) Date of Patent: Jun. 2, 2026

(54) USE OF COMBRETUM MICRANTHUM EXTRACT IN COSMETICS

(71) Applicant: ACADERMA ASIA LIMITED, Hong Kong (CN)

(72) Inventors: Shuting Hu, Hong Kong (CN); James E. Simon, Hong Kong (CN); Yizhen Wu, Hong Kong (CN); Mingfu Wang, Hong Kong (CN); Qingli Wu, Hong Kong (CN)

(73) Assignee: ACADERMA ASIA LIMITED, Hong Kong (CN)

( * ) Notice: Subject to any disclaimer, the term of this patent is extended or adjusted under 35 U.S.C. 154(b) by 1020 days.

(21) Appl. No.: 17/275,087

(22) PCT Filed: Sep. 10, 2019

(86) PCT No.: PCT/CN2019/105221
§ 371 (c)(1),
(2) Date: Mar. 10, 2021

(87) PCT Pub. No.: WO2020/052571
PCT Pub. Date: Mar. 19, 2020

(65) Prior Publication Data
US 2022/0040083 A1 Feb. 10, 2022

(30) Foreign Application Priority Data

Sep. 10, 2018 (CN) .......................... 201811052460.3

(51) Int. Cl.
| | |
|---|---|
| *A61K 8/9789* | (2017.01) |
| *A61K 36/185* | (2006.01) |
| *A61Q 17/04* | (2006.01) |
| *A61Q 19/00* | (2006.01) |
| *A61Q 19/02* | (2006.01) |
| *A61Q 19/08* | (2006.01) |

(52) U.S. Cl.
CPC .......... *A61K 8/9789* (2017.08); *A61K 36/185* (2013.01); *A61Q 17/04* (2013.01); *A61Q 19/004* (2013.01); *A61Q 19/02* (2013.01); *A61Q 19/08* (2013.01); *A61K 2236/333* (2013.01)

(58) Field of Classification Search
CPC ............... A61K 8/9789; A61K 36/185; A61K 2236/333; A61Q 17/04; A61Q 19/004; A61Q 19/02; A61Q 19/08; A61Q 9/02; A61Q 19/00; A61P 17/18; A61P 17/00
See application file for complete search history.

(56) References Cited

U.S. PATENT DOCUMENTS

| | | | | |
|---|---|---|---|---|
| 2008/0294026 A1* | 11/2008 | Arbault | .................. | A61B 5/442 |
| | | | | 600/345 |
| 2011/0182835 A1* | 7/2011 | Caetano | ................. | A61Q 19/08 |
| | | | | 424/59 |
| 2013/0302279 A1 | 11/2013 | Simon et al. | | |
| 2016/0177234 A1 | 6/2016 | Mbengue | | |

FOREIGN PATENT DOCUMENTS

| | | |
|---|---|---|
| CN | 104606122 A | 5/2015 |
| WO | WO2011140066 A1 | 11/2011 |

OTHER PUBLICATIONS

Olajide et al., Evaluation of the anti-inflammatory property of the extract of Combretum micranthum G. Don(Combretaceae). Inflammopharmacology, 11,3, Dec. 31, 2003, pp. 293-298.
Welch et al., Bioactive polyphenols in kinkelibatea (*Combretum micranthum*) and their glucose-lowering activities: PubMed, Journal of Food and Drug Analysis (2017), http://dx.doi.org/10.1016/i.ifda.2017.05.009, 10 pages.
Kaizhen, Modern Women's Guide to Rational Drug Use, People's Medical Publishing House (Beijing), 2001, p. 102.
Chapter X. Plant tannins, Natural Polymer Materials. Huazhong University of Science and Technology Press (Wuhan), 2015, p. 353.
Welch, Cara Renae; Chemistry and Pharmacology of Kinkéliba (*Combretum micranthum*), a West African Midicinal Plant,: Rutgers the State Unviersity of New Jersey—New Brunswick; Jan. 30, 2010, 283 pages.
Miao, Jianhua et al., "Combretum Micranthum"; Southern and Pan-southern Mdicine, Aug. 30, 2014; 3 pages.
Wu, Xiaopeng, "Research Advances in the Chemical Constituents and Pharmacological Functions of Combretum," Journal of Hainan Normal University (Natural Science), Mar. 30, 2007, pp. 63-67.
A. U. Ogan, *The Alkaloids in the Leaves of Combretum Micranthum*, Department of Biochemistry, University of Nigeria, Nsukka, Nigeria, Studies on West African Medicinal Plants. Part VIII, pp. 210-217.
GNDP MINTEL Moisturising Repair Balm, Publication No. XP002735902, 2010.
Duennfluessige Peg-Freie O/W-Emulsionen, Research Disclosure, Jan. 1, 2001 Kenneth Mason Publications, Hampshire, UK, GB, Publication No. XP001127948, Nr:441,pp. 36-38.

(Continued)

*Primary Examiner* — Snigdha Maewall
(74) *Attorney, Agent, or Firm* — NKL Law; Bin Lu

(57) ABSTRACT

A use of *Combretum micranthum* extract in cosmetics. Processes such as a solvent extraction method and a chromatographic method are specifically used, it is found that a *Combretum micranthum* plant or its extract has the effects of moisturizing, anti-inflammatory, post-sun repair, repair of skin barrier, repair of UV-induced DNA damage, skin-lightening, fading spots and anti-glycation and the like. The prepared *Combretum micranthum* extract can be added into cosmetics as an active ingredient thereof. The cosmetic or drug containing the *Combretum micranthum* extract has the efficacies of moisturizing, anti-inflammatory, post-sun repair, repair of skin barrier, repair of UV-induced DNA damage, skin-lightening, anti-freckle and resisting saccharification and the like, thereby achieving the effect of skin care and beauty.

9 Claims, 3 Drawing Sheets

(56)                    References Cited

OTHER PUBLICATIONS

Touré Alhassane, Xu Xueming, Michel T and Bangoura M, *In-vitro antioxidant and radical scavenging of Guinean kinkeliba leaf (Combretum micranthum G. Don) extracts*, Natural Product Research, Jul. 1, 2011 Taylor and Francis Health Sciences, Abingdon, GB, Publication No. XP9535830A, vol. 25,Nr:11,pp. 1025-1036.

Wu Xiaopeng, *Research advances in the chemical constituents and pharmacological functions of Combretum*, Journal of Hainan Normal University(Natural Science), vol. 20 No. 1, 2007.

Huang Youyi, "Tea Microbial Products", China Light Industry Press, p. 217, Aug. 2017, 3 pages.

Zou Xinqiu, "Wuyi Zhengshan Black Tea, the Ancestor of World Black Tea", China Agricultural Press, p. 131, May 2006, 3 pages.

Wang Changtao et al., "Development and Application of Cosmetic Plant Additives", China Light Industry Press, pp. 22-23, Apr. 2013, 4 pages.

Mintel Database, Lancaster, Specific Sun Body Sculpt SPF 15, Published Jun. 2004.†

Mintel Database, Trimar, Qiriness Anti-Brown Spot Serum, Published May 2013.†

Mintel Database, Trimar, Qiriness Hydra-Fraicheur—Moisturizing Sorbet Cream, Published Nov. 2013.†

* cited by examiner
† cited by third party

USE OF COMBRETUM MICRANTHUM EXTRACT IN COSMETICS

TECHNICAL FIELD

The present invention relates to the field of cosmetics and medicine, and in particular to the use of *Combretum micranthum* extract in cosmetics.

BACKGROUND

Cosmetics are a huge demand for modern people's lives. Cosmetics refer to daily chemical industrial products that are applied to human skin, hair, lips, etc. in different ways such as coating, rubbing, and spraying so as to clean, protect, beautify, and promote physical and mental happiness. With the progress of society, people have a deeper understanding of the side effects of chemical synthetic cosmetics, and are more inclined to choose safe and natural cosmetics derived from animals and plants.

Natural cosmetics refer to cosmetics made from ingredients extracted from natural plant extracts. However, the effect of cosmetics containing natural plant extracts on the market is not significant.

Therefore, there is an urgent need in this field to develop a new safe and effective skin care natural cosmetics.

SUMMARY OF INVENTION

The purpose of the present invention is to provide a new safe and effective skin care natural cosmetic.

Another purpose of the present invention is to provide a new use of the extract of *Combretum micranthum* in medicine or cosmetics.

In the first aspect of the present invention, it provides a use of *Combretum micranthum* plant, or botanical raw material, or the extract thereof, for preparing a pharmaceutical or cosmetic composition, wherein the pharmaceutical or cosmetic composition is used for post-sun repair, anti-inflammatory, moisturizing, repair of skin barrier, repair of UV-induced DNA damage, skin-lightening, anti-freckle, anti-glycation, or a combination thereof.

In another preferred embodiment, the post-sun repair comprises repair of UV-induced cell damage, repair of UV-induced acute erythema, or a combination thereof.

In another preferred embodiment, the anti-inflammatory comprises inhibiting production of IL-6 and/or IL-8.

In another preferred embodiment, the UV or ultraviolet is selected from the group consisting of UVA, UVB, and combinations thereof.

In another preferred embodiment, the cell is epidermal cell.

In another preferred embodiment, the epidermal cells comprise keratinocytes, dendritic cells, and combinations thereof.

In another preferred embodiment, the pharmaceutical or cosmetic composition is used for anti-aging and/or anti-oxidation.

In another preferred embodiment, the extract of *Combretum micranthum* comprises water-soluble and/or lipid-soluble extracts of branches, leaves, roots, flowers, fruits and/or stems of *Combretum micranthum* plant or a plant of the same genus.

In another preferred embodiment, the extract of *Combretum micranthum* comprises a water extract, an aqueous solvent extract, an alcohol extract, and combinations thereof.

In another preferred embodiment, the extract of *Combretum micranthum* is an extract of leaves.

In another preferred embodiment, the extract of *Combretum micranthum* is a water-soluble extract of leaves of *Combretum micranthum* plant or a plant of the same genus.

In another preferred embodiment, the extract contains one or more components selected from the group consisting of polysaccharides (such as water-soluble polysaccharides), plant polyphenols, polyphenol glycosides, and combinations thereof.

In another preferred embodiment, the extract is obtained by solvent separation, extraction, and/or chromatography.

In another preferred embodiment, an extractant for the extract is selected from the group consisting of water, alcohol (preferably C1-C4 alcohol, such as methanol, ethanol, propanol), aqueous solvent, and any mixture thereof.

In another preferred embodiment, the extract is obtained by the extraction method of the present invention.

In another preferred embodiment, the pharmaceutical or cosmetic composition further comprises an additional component selected from the group consisting of skin-lightening or anti-freckle component, anti-inflammatory component, antioxidant component, anti-ultraviolet component, and a combination thereof.

In another preferred embodiment, the pharmaceutical composition comprises powder, granule, capsule, injection, tincture, oral liquid, tablet or lozenge.

In another preferred embodiment, the formulation of the cosmetic composition is a solid formulation, a semi-solid formulation, or a liquid formulation, such as a solution, gel, cream, lotion, ointment, cream, paste, cake, powder, patch, etc.

In the second aspect of the present invention, it provides an effective part useful for preparing a pharmaceutical or cosmetic composition, wherein the effective part has the following features:

(a) the effective part is a water-soluble, lipid-soluble, and/or alcoholic extract extracted from branches, leaves, roots, flowers, fruits and/or stems of *Combretum micranthum;*

(b) the effective part has an effect selected from the group consisting of moisturizing, anti-inflammatory, post-sun repair, repair of skin barrier, repair of UV-induced DNA damage, skin-lightening, anti-freckle, anti-glycation, and combinations thereof.

In another preferred embodiment, the effective part is used for anti-aging and/or anti-oxidation.

In another preferred embodiment, the effective part contains one or more components selected from the group consisting of polysaccharides (such as water-soluble polysaccharides), plant polyphenols, polyphenol glycosides, and combinations thereof.

In another preferred embodiment, the effective part is obtained by solvent extraction, extraction, and/or chromatography.

In another preferred embodiment, an extractant for the effective part is selected from the group consisting of water, alcohol (preferably C1-C4 alcohol, such as methanol, ethanol, propanol), aqueous solvent, and any mixture thereof.

In another preferred embodiment, the effective part is extracted by the extraction method of the present invention.

In the third aspect of the present invention, it provides a pharmaceutical or cosmetic composition, which comprises (a) an effective part of the second aspect of the present invention; and (b) a pharmaceutically or cosmetically acceptable carrier or excipient.

In another preferred embodiment, the pharmaceutical or cosmetic composition is used for moisturizing, anti-inflammatory, post-sun repair, repair of skin barrier, repair of UV-induced DNA damage, skin-lightening, anti-freckle, anti-glycation, and combinations thereof.

In another preferred embodiment, the pharmaceutical or cosmetic composition is used for anti-aging and/or anti-oxidation.

In another preferred embodiment, in the cosmetic composition, the mass percentage of the (dry) effective part is 0.0001-15 wt %, preferably 0.0001-10 wt %, and preferably 0.001-5 wt %, calculated based on the total weight of the cosmetic composition.

In another preferred embodiment, in the pharmaceutical composition, the mass percentage of the (dry) effective part is 0.001-50 wt %, preferably 0.01-20 wt %, calculated based the total weight of the pharmaceutical composition.

In another preferred embodiment, the pharmaceutical or cosmetic composition further comprises an additional component selected from the group consisting of skin-lightening or anti-freckle component, anti-inflammatory component, antioxidant component, anti-ultraviolet component, and combinations thereof.

In another preferred embodiment, the cosmetically acceptable carrier or excipient is selected from the group consisting of moisturizer, antioxidant, anti-ultraviolet agent, preservative, film-forming agent, oil-soluble gelling agent, organically modified clay minerals, resins, antibacterial agents, essences, salts, pH regulators, chelating agents, cooling agents, anti-inflammatory agents, skin beautification ingredients, vitamins, amino acids, nucleic acids, hormones, inclusion compounds, and combinations thereof.

In another preferred embodiment, the pharmaceutical composition comprises powder, granule, capsule, injection, tincture, oral liquid, tablet or lozenge.

In another preferred embodiment, the formulation of the cosmetic composition is a solid formulation, a semi-solid formulation, or a liquid formulation, such as a solution, gel, cream, lotion, ointment, cream, paste, cake, powder, patch, etc.

In another preferred embodiment, the cosmetic composition is used for skin care and beauty, sun-screening, or post-sun repair.

In another preferred embodiment, the cosmetic composition contains the effective part (the extract of *Combretum micranthum*) according to the second aspect of the present invention as an effective ingredient.

In the fourth aspect of the present invention, it provides a method for preparing a pharmaceutical or cosmetic composition, comprising a step of mixing the effective part of the second aspect of the present invention with a pharmaceutically or cosmetically acceptable carrier, thereby forming the pharmaceutical or cosmetic composition.

It should be understood that in the present invention, any of the technical features specifically described above and below (such as in the Examples) can be combined with each other to form a new or preferred technical solution which will not redundantly be described one by one herein.

DETAILED DESCRIPTION OF THE INVENTION

Figure 1:
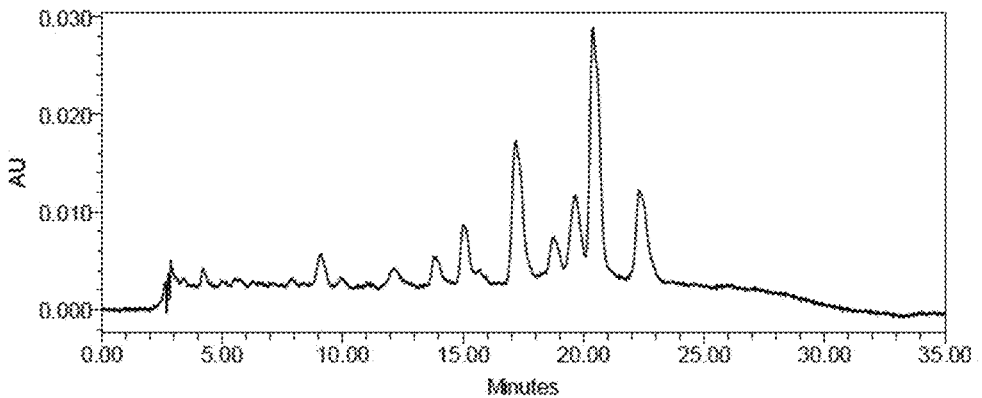
FIG. 1 shows the HPLC profile of the extract prepared by the method 1.7 in Example 1.

After extensive and intensive researches, the inventor have firstly and unexpectedly discovered that the *Combretum micranthum* plant, botanical raw material, or the extract thereof can be used in medicine or cosmetics (such as skin care products). Specifically, the inventors used solvent separation, solvent extraction, chromatography or other processes, and found that the *Combretum micranthum* plant or its extract has the effects such as moisturizing, anti-inflammatory, post-sun repair, repair of skin barrier, repair of UV-induced DNA damage, skin-lightening, anti-freckle, anti-glycation, and the like. The extract of *Combretum micranthum* prepared by the present invention can be added into cosmetics as an active ingredient. The cosmetics or medicine comprising the extract of *Combretum micranthum* has the effects of moisturizing, anti-inflammatory, post-sun repair, repair of skin barrier, repairing ultraviolet-induced DNA damage, skin-lightening, anti-freckle, anti-glycation, etc., thereby achieving the effects of skin care and beauty. The present invention has been completed on this basis.

*Combretum micranthum*

*Combretum micranthum* (also known as kinkeliba), is a non-domesticated shrub species found in the jungle of West Africa. It is a dense shrub or vine, commonly found in cultivated and fallow fields, mainly located in sub-Saharan Africa, with higher yields in Senegal, *Mali* and Burkina Faso. In several tropical West African savannah countries, people get the leaves from *Combretum micranthum* of wild populations as a popular traditional herbal tea. As a shrub tea, *Combretum micranthum* has a pleasant taste, and the soup thereof has a color of light to dark greenish brown. The shrub tea is also used locally as a traditional panacea useful for promoting diuresis and alleviating digestive problems such as gastrointestinal problems, colic and vomiting.

In previous phytochemical studies, it has found that the extract of *Combretum micranthum* is rich in flavonoids, including vitexin, isovitexin, orientin, homoorientin, myricetin-3-O-glucoside and myricetin-3-O-rutinoside; alkaloids including stachytine, hydroxystachyline and choline; and sugar alcohols, including meta-inositol and sorbitol; and flavanoid alkaloids, including kinkeloids A, B, C and D. It has been reported that the flavonoids contained in the ethyl acetate extract of *Combretum micranthum* have hypoglycemic activity.

In the present invention, it is found for the first time that the *Combretum micranthum* plant or its extract has the effects of moisturizing, anti-inflammatory, post-sun repair, repair of skin barrier, repair of UV-induced DNA damage, skin-lightening, anti-freckle, anti-glycation and the like. The extract of *Combretum micranthum* prepared by the present invention can be added into cosmetics as an effective ingredient.

Effective Part

As used herein, the terms "extract of the present invention" and "effective part of the present invention" are used interchangeably, and both refer to the extract from the *Combretum micranthum* plant, which has the effects of moisturizing, anti-inflammatory, post-sun repair, repair of skin barrier, repair of UV-induced DNA damage, skin-lightening, anti-freckle, anti-glycation and the like.

In the present invention, the effective part of the present invention can be extracted from the *Combretum micranthum* plant as a raw material.

In addition, although the effective part of the present invention may be derived from the whole plant of the *Combretum micranthum*, it is preferably extracted from the above-ground parts of *Combretum micranthum* plant, such as leaves and the like.

As used herein, the term "extract" or "effective part" includes water-soluble and/or lipid-soluble extracts. The term also includes alcohol extracts, or water extracts, or aqueous solvent extracts. In addition, it also includes a group of effective parts, that is, an extract or a mixture containing a lipid-soluble effective part and a water-soluble effective part.

As used herein, "water-soluble extract" refers to an extract that is soluble in a polar solvent (preferably, water).

In another preferred embodiment, the extract of the present invention is obtained by the extraction method of the present invention.

According to analysis, the chemical components contained in the effective part of the present invention include at least one or more substances selected from the group consisting of polysaccharides (such as water-soluble polysaccharides), plant polyphenols, polyphenol glycosides, and combinations thereof. The effective part of the present invention has the effects of moisturizing, anti-inflammatory, post-sun repair, repair of skin barrier, repair of UV-induced DNA damage, skin-lightening, anti-freckle, anti-glycation and the like.

According to analysis, the total polyphenol contained in the effective part of the present invention is ≥1 wt %, preferably ≥5 wt %, and is more preferably, 5-80 wt %, more preferably, 10-75 wt %, and most preferably, 15-70 wt %, calculated based on the dry weight of the effective part.

In an embodiment of the present invention, the extract has the HPLC profile shown in FIG. 1.

There is no particular limitation on the method that can be used to prepare *Combretum micranthum* extract of the invention. Conventional methods can be utilized to obtain water-soluble and/or lipid-soluble extracts by using *Combretum micranthum* plants as raw materials.

In a preferred embodiment of the present invention, the preparation of the effective part is carried out by solvent separation, extraction, supercritical extraction and/or chromatography.

In the present invention, the extraction can be proceed one or more times (such as twice, 3 times, 4 times, 5 times). When multiple extraction is carried out, the multiple extracts can be combined for subsequent processing.

In the present invention, there is no particular limitation on solvents used for solvent separation. The representative examples include (but are not limited to): water, ethanol, methanol, and aqueous solvents, and any mixtures thereof.

In the present invention, an aqueous solvent refers to a mixed solvent formed by water and other solvents such as alcohols (especially C1-C4 alcohols such as ethanol and propanol). Generally, in the aqueous solvent, the content of the alcohol solvent is 0.01-80 wt %, preferably 5-60 wt %, and more preferably 10-30 wt %, based on the total weight of the aqueous solvent.

In the present invention, there is no particular limitation on solvents used for solvent extraction. The representative examples include (but are not limited to): n-butanol, dichloromethane, chloroform, C5-C7 alkanes, cyclohexane, petroleum, and any mixtures thereof. The extractions can be proceeded one or more times.

In the present invention, there is no particular limitation on solvents used for supercritical extraction. The representative examples include (but are not limited to) carbon dioxide or propane.

In the present invention, there is no particular limitation on columns useful for column chromatography. The representative examples include (but are not limited to): activated carbon, silica gel, reverse phase silica gel, macroporous resin, dextran gel, or a combination thereof.

In a preferred embodiment of the present invention, the leaves (dried or fresh leaves) of *Combretum micranthum* plants are used as raw materials, and a sufficient amount of water (such as 5-200 times in weight) or aqueous solvent is used to extract 1-5 times, thereby obtain an aqueous extract. In addition, in the present invention, the lipid-soluble components can be further separated (or removed) from the aqueous extract, so as to obtain a *Combretum micranthum* extract with a higher content (or relative content) of water-soluble components, or a *Combretum micranthum* extract which mainly contain water-soluble components.

In the present invention, a preferred method for removing lipid-soluble components comprises: extracting the extract with a lipid-soluble solvent (such as ethyl acetate, hexane, etc.), so that the residual aqueous solution after extraction with the lipid-soluble solvent is a preferred effective part. According to test, said effective part has significantly low cytotoxicity or no cytotoxicity.

In an embodiment of the present invention, the extraction method comprises the following steps:

a. providing *Combretum micranthum*, preferably leaves thereof;

b. extracting *Combretum micranthum* with an extractant;

c. optionally removing at least partial extractant, thereby obtaining a concentrated extract;

d. optional removing the lipid-soluble components from the extract;

e. optionally removing at least partial extractant, thereby obtaining a concentrated extract;

f. optionally drying so as to obtain the extract.

In another preferred embodiment, the extractant is water, ethanol, methanol, aqueous solvent, or any mixtures thereof.

In another preferred embodiment, the extraction in step b is proceeded one or more times.

In another preferred embodiment, the extraction is carried out under 5-100° C. (preferably 20-95° C.).

In another preferred embodiment, the drying is spray drying or vacuum drying (such as vacuum freeze drying).

Application

As used herein, the term "pharmaceutical or cosmetic composition" comprises (a) the effective part of the present invention; and (b) a pharmaceutically or cosmetically acceptable carrier or excipient. In addition, the pharmaceutical composition also comprises a health care product composition, and the cosmetic composition comprises a skin care product.

The *Combretum micranthum* extract of the present invention may be prepared into a pharmaceutical composition, which can be a formulation such as tablets, capsules, powders, granules, solutions, lozenges, jellies, cream preparations, syrups, suspensions, tinctures, mud dressings, liniment, lotions, aerosols, and the like. The medicine can be prepared by generally known preparation techniques, and suitable pharmaceutical additives can be added into the medicine.

Examples of pharmaceutical additives include excipients, binders, decomposers, lubricants, flow aids, suspending agents, emulsifiers, stabilizers, moisturizers (wetting agents), preservatives, solvents, solubilizers, preservatives, flavoring agent, sweeteners, dyes, fragrances, propellants, etc. These pharmaceutical additives can be selected and added in an appropriate amount within a range that does not affect the effects of the present invention.

The *Combretum micranthum* extract of the present invention may be prepared into a cosmetic composition, which can be a formulation such as emulsion, liquid, ointment, cream, paste, cake, powder, and the like.

To the extent that the effects of the present invention are not hindered, other ingredients commonly used in cosmetics may be added into the cosmetics of the present invention, such as film formers, oil-soluble gelling agents, organically modified clay minerals, resins, moisturizers, preservatives, antibacterial agents, flavors, salts, antioxidants, pH adjusters, chelating agents, cooling agents, anti-inflammatory agents, ingredients for skin beautification (skin-lightening agents, cytoactive agents, skin roughness improving agents, blood circulation promoters, skin firming agents, anti-lipid leakage agents, etc.), vitamins, amino acids, nucleic acids, hormones, inclusion compounds, etc.

The oil-soluble gelling agent is selected from metal soaps such as aluminum stearate, magnesium stearate, and zinc myristate; amino acid derivatives such as N-lauroyl-L-glutamic acid, α,γ-di-n-butylamine; cyclodextrin fatty acid esters such as cyclodextrin palmitate, cyclodextrin stearate, and cyclodextrin 2-ethylhexanoic acid palmitate; sucrose fatty acid esters such as sucrose palmitate and sucrose stearate; benzylidene derivatives of sorbitol such as monobenzylidene sorbitol and dibenzylidene sorbitol; gelling agent of organically modified clay minerals such as dimethylbenzyldodecylammonium montmorillonite clay and dimethyldioctadecylammonium montmorillonite clay. One, two or more types of agents may be used as required.

Humectants include glycerin, sorbitol, propylene glycol, dipropylene glycol, 1,3-butanediol, glucose, xylitol, maltitol, polyethylene glycol, hyaluronic acid, chondroitin sulfate, pyrrolidone carboxylate, polyoxyethylene methyl glucoside, polyoxypropylene methyl glucoside, etc.

Antibacterial preservatives include alkyl p-hydroxybenzoate, benzoic acid, sodium benzoate, sorbic acid, potassium sorbate, phenoxyethanol, etc., Antibacterial agents include benzoic acid, salicylic acid, carbolic acid, sorbic acid, alkyl p-hydroxybenzoate, p-chloro-m-cresol, hexachlorophenol, benzalkonium chloride, chlorhexidine chloride, trichloro-N-carbanilide, triclosan, photosensitizer, phenoxyethanol, etc.

Antioxidants include tocopherol, butylhydroxyanisole, dibutylhydroxytoluene, phytic acid, etc. PH regulators include lactic acid, citric acid, glycolic acid, succinic acid, tartaric acid, dl-malic acid, potassium carbonate, sodium bicarbonate, ammonium bicarbonate, etc Chelating agents include alanine, sodium ethylenediaminetetraacetate, sodium polyphosphate, sodium metaphosphate, phosphoric acid, etc. Cooling agents include L-menthol, camphor, etc. Anti-inflammatory agents include allantoin, glycyrrhetinic acid, glycyrrhizic acid, tranexamic acid, azulene, etc.

Ingredients for skin beautification include skin-lightening agents such as placenta extract, arbutin, glutathione and saxifrage extract; cytoactive agents such as royal jelly, photoreceptor, cholesterol derivatives, calf blood extract; skin roughness improving agents; blood circulation promoters such as valeramide pelargonate, benzyl nicotinate, β-butoxyethyl nicotinate, capsaicin, gingerone, cantharidin tincture, ichthyol, caffeine, tannic acid, α-borneol, tocopherol nicotinate, inositol hexanicotinate, cyclomandelate, cinnarizine, tolazoline, acetylcholine, verapamil, stephane and γ-oryzanol; skin firming agents such as zinc oxide, tannic acid; anti-lipid leakage agents such as sulfur. Vitamins include vitamin A such as vitamin A oil, rosin oil, rosin acetate, rosin palmitate; vitamin B2 such as riboflavin, riboflavin butyrate and flavin adenine nucleotides; vitamin B6 such as pyridoxine hydrochloride, pyridoxine dicaprylate, pyridoxine tripalmitate, vitamin B such as vitamin B12 and its derivatives, vitamin B15 and its derivatives; vitamin C such as L-ascorbic acid, L-ascorbyl dipalmitate, sodium L-ascorbate-2-sulfate and dipotassium L-ascorbate phosphate; vitamin D such as ergocalciferol and cholecalciferol; vitamin E such as α-tocopherol, β-tocopherol, γ-tocopherol, dl-α-tocopherol acetate, dl-α-tocopherol nicotinic acid, dl-α-tocopherol succinate; vitamin H; vitamin P; niacin such as nicotinic acid, benzyl nicotinate, niacinamide; pantothenic acid such as calcium pantothenate, D-panthenol, pantothen ethyl ether and acetyl pantothen ethyl ether; biotin and the like.

Amino acids include glycine, valine, leucine, isoleucine, serine, threonine, phenylalanine, arginine, lysine, aspartic acid, glutamic acid, cystine, cysteine, methionine and tryptophan. Nucleic acids include deoxyribonucleic acid and the like, and hormones include estradiol, vinyl estradiol and the like.

Preferred enbodiments of the cosmetics of the present invention include skin care cosmetics, make-up cosmetics, and anti-ultraviolet cosmetics. For example, the basic cosmetics comprise, e.g., lotions, creams, lotions, sunscreens, mask materials, facial cleansers, and essences; and make-up cosmetics comprise, e.g., foundations, white powders, and blushes.

There is no particular limitation on the form of the product, and it may be liquid, emulsion, cream, solid, paste, gel, powder, multilayer, mousse, spray, and the like.

The present invention also provides a skin care method, which comprises a step of: administering the *Combretum micranthum* extract of the present invention or the composition of the present invention to an subject in need.

In another preferred embodiment, the effective concentration range of the extract of *Combretum micranthum* is 100 μg/ml-500 mg/ml.

In another preferred embodiment, the method is for moisturizing, anti-inflammatory, post-sun repair, repair of skin barrier, repair of UV-induced DNA damage, skin-lightening, anti-freckle, anti-glycation and the like.

In the present invention, the applications such as post-sun repair, repair of skin barrier, repair of UV-induced DNA damage, etc. include both preventive applications and post-improving applications. For example, for post-sun repair, it includes applying the *Combretum micranthum* extract or composition of the present invention before, during, and/or after exposing to the sun, thereby performing post-sun repair.

The Main Advantages of the Invention Include:

(A) It is for the first time discovered that the *Combretum micranthum* can have significant effects on human body (such as epidermis), including moisturizing, anti-inflammatory, post-sun repair, repair skin barrier, repair UV-induced DNA damage, whiten, anti-freckle, and anti-glycation. This discovery has a great significance for developing new cosmetics or medicines.

(b) The *Combretum micranthum* plant has been widely used for a long time. It is a dual-purpose plant for medicine and food, and it is a safe and common herbal material with low toxicity and side effects.

(c) The process for preparing the effective part is simple and practical, and the obtained effective part can have significant effects at a low concentration, including moisturizing, anti-inflammatory, post-sun repair, repair skin barrier, repair UV-induced DNA damage, whiten, anti-freckle, and anti-glycation.

The present invention will be further explained below in conjunction with specific embodiments. It should be understood that these embodiments are only used to illustrate the present invention and not to limit the scope of the present invention. The experimental methods that do not indicate specific conditions in the following examples usually follow the conventional conditions or the conditions suggested by the manufacturer. Unless otherwise specified, percentages and parts are percentages by weight and parts by weight.

Example 1 Method for Preparing *Combretum micranthum* Extract 1.1 500 g (dry weight) of leaves of *Combretum micranthum* were taken, and soaked at 85-100° C. for 30-60 min after enough water was added,. If necessary, adding water and soaking were repeated 1-4 times and the extracts were combined. The extract was concentrated to ⅓-¼ of the original volume. Ethyl acetate was added, then the ethyl acetate phase was removed after extraction, and the aqueous phase was collected. The aqueous phase was concentrated under reduced pressure and lyophilized into powder for use.

1.2 The leaves were extracted by 95% refluxing ethanol (1:5-1:20) three times, each time for 1 h. Three extracts were combined and concentrated under reduced pressure until there was no ethanol, thereby obtaining a crude extract (paste) of *Combretum micranthum*. To the crude extract of *Combretum micranthum* was added purified water (1:1). The mixture was suspended with ultrasonic, transferred into a suitable separatory funnel, and then successively extracted with petroleum ether, ethyl acetate, and n-butanol (3 times with each solvent), respectively. The petroleum ether layer solution, ethyl acetate layer solution, n-butanol layer solution and aqueous solution were combined, respectively, and concentrated under reduced pressure to obtain four types of crude extract.

1.3 The leaves were soaked with 95% ethanol (1:5-1:20) three times at room temperature and 24 h each time. Three extracts were combined and concentrated under reduced pressure until there was no ethanol, thereby obtaining a crude extract (paste) of *Combretum micranthum*. To the crude extract of *Combretum micranthum* was added purified water (1:1). The mixture was suspended with ultrasonic, transferred to a suitable separatory funnel, and then successively extracted with petroleum ether, ethyl acetate, and n-butanol (3 times for each solvent), respectively. The petroleum ether layer solution, ethyl acetate layer solution, n-butanol layer solution and aqueous solution were combined, respectively, and concentrated under reduced pressure to obtain four types of crude extract.

1.4 The leaves were extracted by refluxing water (1:5-1:20) three times and 1 h each time. Three extracts were combined and concentrated under reduced pressure to ¼ of the original volume to obtain the crude extract concentrate of *Combretum micranthum*, which was transferred into a suitable separatory funnel, and then successively extracted with petroleum ether, ethyl acetate, and n-butanol (3 times for each solvent), respectively. The petroleum ether layer solution, ethyl acetate layer solution, n-butanol layer solution and aqueous solution were combined, respectively, and concentrated under reduced pressure to obtain four types of crude extract.

1.5 The leaves were soaked with water (1:5-1:20) at room temperature three times and 24 h each time. Three extracts were combined and concentrated under reduced pressure to ¼ of the original volume to obtain the crude extract concentrate of *Combretum micranthum*, which was transferred into a suitable separatory funnel, and then successively extracted with petroleum ether, ethyl acetate, and n-butanol (3 times for each solvent), respectively. The petroleum ether layer solution, ethyl acetate layer solution, n-butanol layer solution and aqueous solution were combined, respectively, and concentrated under reduced pressure to obtain four types of crude extract.

1.6 The leaves were soaked with boiling water (1:50-1: 100) three times and 10-60 min each time. Three extracts were combined and concentrated under reduced pressure to ¼ of the original volume to obtain the crude extract concentrate of *Combretum micranthum*, which was transferred into a suitable separatory funnel, and then successively extracted with petroleum ether, ethyl acetate, and n-butanol (3 times for each solvent), respectively. The petroleum ether layer solution, ethyl acetate layer solution, n-butanol layer solution and aqueous solution were combined, respectively, and concentrated under reduced pressure to obtain four types of crude extract.

1.7 The dried leaves of *Combretum micranthum* were soaked with boiling water (1:50-1:100) for 10-60 minutes, and the soaking was repeated 1-3 times. The water solution was combined and cooled to room temperature. The water solution was concentrated by rotary evaporation. Then it was successively extracted with ethyl acetate and n-hexane, the water layer was collected and evaporated in vacuo to a required amount, freeze-dried, and stored at room temperature under anhydrous conditions for analysis.

1.8 The dried leaves of *Combretum micranthum* (20 g) were soaked with boiling water (1:10-1:50) for 5-60 minutes. After the water solution was cooled to room temperature, the filtered extract was loaded onto a macroporous resin column, and then the same volume of purified water, the same volume of 70% ethanol were loaded onto the macroporous resin column. The solution containing the effective part was collected, and the collected extract was dried by rotation to obtain a concentrated solution. The concentrated solution was placed into a powder spray dryer. After drying, a dry powder was obtained, and stored at room temperature under anhydrous conditions for analysis.

1.9 The dried leaves (1.0 kg) were grinded into fine powder and extracted twice with ethanol, and the third extraction was soaked with 80% (v/v) ethanol solution for 24 hours at room temperature. The filtrates were combined and concentrated under reduced pressure. The crude extract was dissolved in water/ethanol (95:5, v/v), and then successively extracted with n-hexane, chloroform, ethyl acetate and n-butanol (3 times for each solvent), respectively, and the n-hexane layer solution, chloroform layer solution, ethyl acetate ester layer solution, n-butanol layer solution and water solution were combined, respectively, and concentrated under reduced pressure to obtain five types of crude extracts.

HPLC analysis was performed on Waters 2695 HPLC system with a DAD detector. The samples for analysis were separated by C18 column chromatography, and the mobile phase was composed of water (A) and acetonitrile (B). Representatively, the extract prepared by the above method 1.7 had a HPLC profile shown in FIG. 1.

Example 2 Effects of Water Extract of *Combretum micranthum*

1. Cell Cultivation, Treatment with Water Extract of *Combretum micranthum* and UVA Irradiation Human protodermal keratinocytes were purchased from the American Type Culture Collection (ATCC) (Rockville, MD, USA). Keratinocytes of passage 1-5 were cultured in dermal cell basal medium at 37° C., 5% $CO_2$. The medium was supplemented with keratinocyte growth kit, which contained 0.4% bovine pituitary extract (BPE), 0.5 ng/mL rhTGF-$\alpha$, 6 mM L-glutamine, 100 ng/mL hydrocortisone, 5 $\mu$g/mL insulin, 1.0 $\mu$M epinephrine and 5 $\mu$g/mL apolipoprotein-transferrin. The water extract of *Combretum micranthum* was diluted to various concentrations and added into the cell culture medium before or after UV irradiation according to different experimental devices. The cells were irradiated with UVP CL-1000L fluorescent lamp (Fisher Scientific, USA) for a total of 4.5 J/cm² UVA. All cells were subjected to same treatment in the whole process. Before irradiation, the cells were washed with PBS, covered with a thin layer of PBS, and irradiated with UVA without a plastic cover. The intensity of UVA irradiation was measured using a UVA-365 radiometer (Lutron Co, Taiwan).

2. Measurement of Cell Viability

Figure 2:
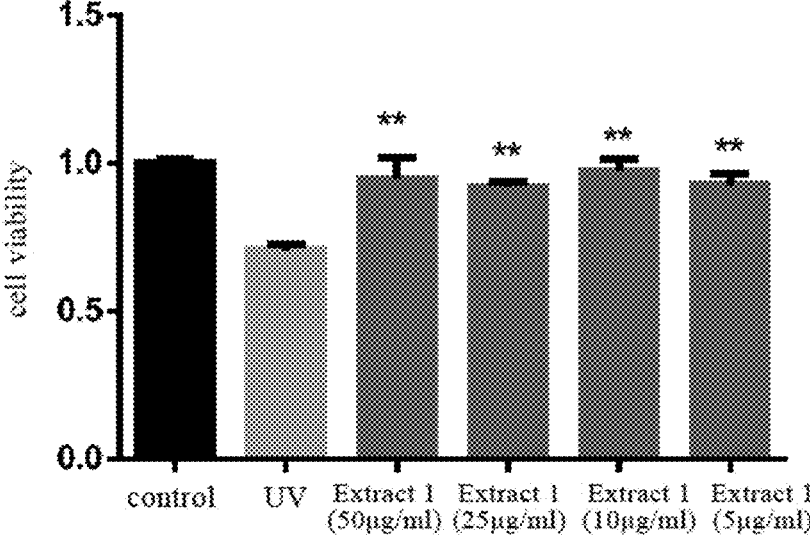
FIG. 2 shows that *Combretum micranthum* extract 1 can significantly improve cell viability.
Figure 3:
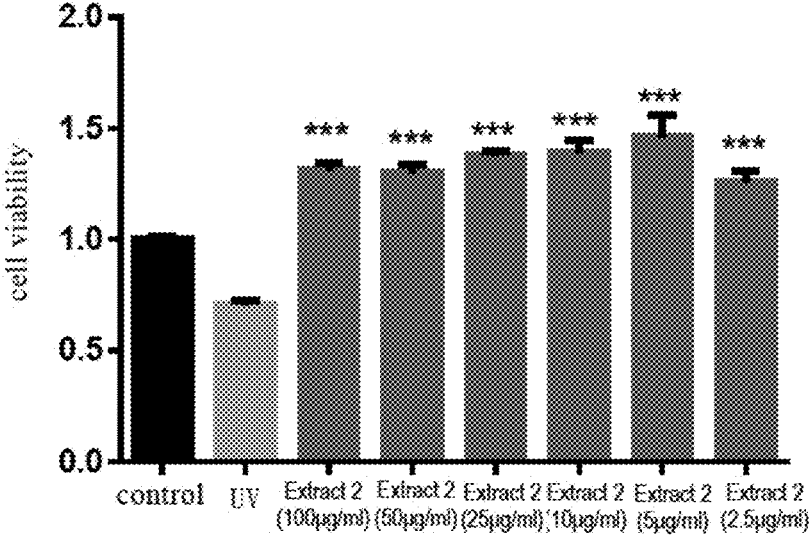
FIG. 3 shows that *Combretum micranthum* extract 2 can significantly improve cell viability.

The cell viability was measured by the CCK-8 assay according to the manufacturer's instructions. After being irradiated by UVA or treated with the water extract of *Combretum micranthum*, the cells were washed three times with PBS. Subsequently, a medium containing 10% CCK-8 solution was added into each well. After 2 hours of incubation, the absorbance was measured at 450 nm using Victor X4 Multilabel Plate Reader (PerkinElmer, MA, USA). The results of the experiment are shown in FIGS. 2-3, where extract 1 is the extract obtained in method 1.8 Example 1, and extract 2 is the extract obtained in method 1.1 of Example 1. From the figures, it can be seen that the extract of *Combretum micranthum* can significantly improve the cell viability, reduce the damage of cells caused by ultraviolet.

3. Cellular Oxidative Stress (ROS) Measurement

The formation of ROS in the cells was assessed by DCFA corrected with the CCK-8 assay to account for the cell loss after UVA radiation. A 96-well plate was seeded at a density of 15,000 keratinocytes per well 24 hours before the test. The HEK cells were pretreated with water extract of *Combretum micranthum* in different concentrations for 24 hours, and then washed three times with PBS before UVA irradiation. After being irradiated with 4.5 J/cm² UVA, 100 $\mu$L of PBS containing DCFA (25 $\mu$M) was added to the cells and incubated at 37° C. for 30 minutes, then the fluorescence measurement of intracellular ROS was conducted. The plate was placed in a Victor X4 Multilabel Plate Reader (PerkinElmer, MA, USA). The fluorescence was monitored using an excitation wavelength of 485 nm and an emission wavelength of 535 nm. The individual absorbance values were corrected with the cell viability determined by the CCK-8 assay before summarized.

Figure 4:
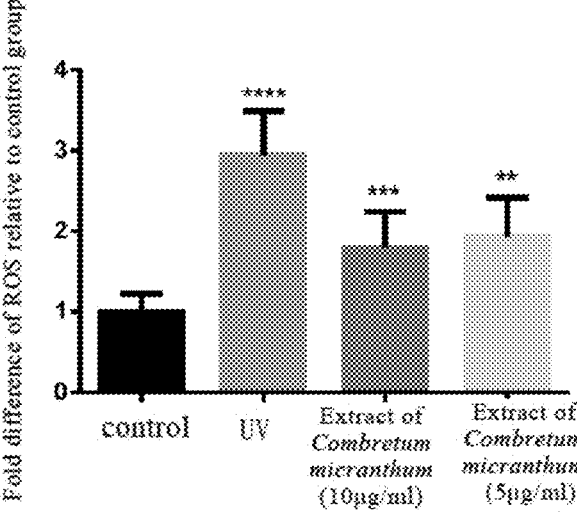
FIG. 4 shows that the water extract of *Combretum micranthum* reduces production of UVA-induced reactive oxygen species (ROS).

Ultraviolet radiation is a main environmental threat to the skin. It causes an increase in photooxidative damage by generating active oxygen. The results are shown in FIG. 4, compared with the control group, the UVA group significantly increased the production of cellular reactive oxygen species. At the same time, pretreatment with *Combretum micranthum* water extract reduced the increased reactive oxygen species induced by UVA. The results show that *Combretum micranthum* has effect of repairing oxidative damage caused by ultraviolet rays, and can delay skin aging.

4. Measurement of Nitrotyrosine

Reagents provided in the competitive ELISA kit ab113848 (Abcam, Cambridge, MA, USA) were used for the detection of nitrotyrosine. 3NT BSA was used as a standard positive control to validate the assay. Briefly, $2\times10^5$/well keratinocytes were seeded in a 24-well plate 24 hours before the test. After UVA irradiation, they were treated with *Combretum micranthum* water extract for 16 hours, and adherent cells were collected by scraping. The cell pellet was dissolved in extraction buffer on ice for 20 minutes. After centrifugation at 4° C. for 20 minutes, the supernatant was collected. Each sample was diluted and adjusted to approximately the same protein concentration via protein concentration determination (Bio-Rad, Hercules, CA). 50 $\mu$l of each diluted standard or sample together with 50 $\mu$L of 2×HRP detection antibody were added to each well of a 96-well microtiter plate coated with nitrotyrosine, and incubated at room temperature for 2 hours. After washing four times, 100 $\mu$L of HRP development solution was added into each well. The OD value was measured according to the manufacturer's instructions. The concentration of nitrotyrosine was calculated from a standard curve generated by 3NT BSA.

Figure 5:
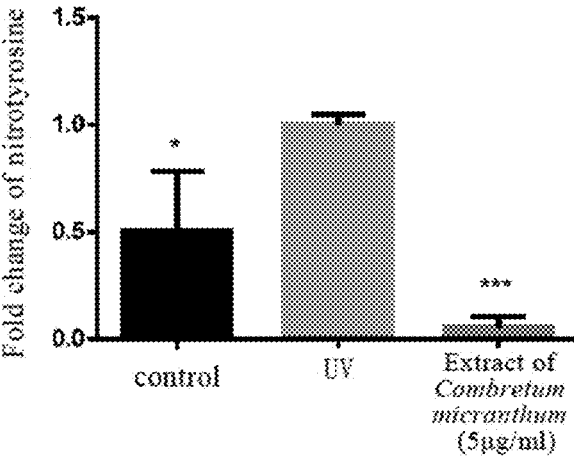
FIG. 5 shows that the water extract of *Combretum micranthum* can resist UVA-induced increase of nitrotyrosine.

The results are shown in FIG. 5. After UVA induction, compared with the control cells, the nitrotyrosine content of the UV group was significantly increased. Compared with the UV group, the level of nitrotyrosine in keratinocytes treated with the water extract of *Combretum micranthum* was significantly reduced, indicating that *Combretum micranthum* had an anti-inflammatory effect.

5. Measurement of 8-OHdG

As one of the byproducts of oxidative DNA damage, 8-OHdG is a ubiquitous oxidative stress factor. An OxiSelect Oxidative DNA Damage ELISA Kit (8-OhdG Quantitation) (Cell Biolabs, San Diego, USA) was used to achieve the measurement of 8-OHdG in DNA samples. Keratinocytes were inoculated in a 6-well plate at a density of $8\times10^5$/well. After 24 hours of incubation, the cells were exposed to 4.5 J/cm² UVA. After irradiation, the cells were incubated at 37° C. for 60 minutes with or without treatment of the water extract of *Combretum micranthum*. Subsequently, the cells were harvested using 0.05% trypsin-EDTA solution. DNA samples were extracted using a DNeasy Blood and Tissue Kit (Qiagen, CA, USA). Each DNA sample was diluted to 40 $\mu$g/mL with cold PBS. Then the DNA samples were incubated at 95° C. for 10 minutes, and quickly cooled on ice for 10 minutes, thereby converting into single-stranded DNA. After incubating with 10 units of nuclease P1 in 20 mM sodium acetate (pH 5.2) at 37° C. for 2 hours, the denatured DNA samples would be digested into nucleosides, and then treated with 5 units of alkaline phosphatase in 100 mM Tris (pH7.5) at 37° C. for 1 hour. The reaction mixture was then centrifuged at 6000 g for 5 minutes, and the supernatant was used for 8-OHdG ELISA assay. The amount of 8-OHdG in each sample was determined by comparing the absorbance with a known standard curve.

6. Measurement of CPD

CPD in DNA samples was detected and quantified by an OxiSelect™ Oxidative UV-induced DNA Damage ELISA kit (Cell Biolabs, San Diego, USA). Keratinocytes were seeded in a 12-well plate at a density of $4\times10^5$/well. After 24 hours of incubation with or without treatment of the water extract of *Combretum micranthum*, the cells were exposed to 4.5 J/cm$^2$ UVA. After irradiation, the cells were incubated with or without treatment at 37° C. for 60 minutes, 90 minutes and 120 minutes. Subsequently, the cells were harvested using 0.05% trypsin-EDTA solution. DNA samples were extracted using a DNeasy Blood and Tissue Kit (Qiagen, CA, USA). Each DNA sample was diluted to 2 µg/mL with cold PBS. Then the DNA sample and CPD-DNA standard were converted into single-stranded DNA by incubating the DNA sample at 95° C. for 10 minutes and rapidly cooling on ice for 10 minutes. 100 µL of denatured DNA samples or CPD-DNA standards diluted with cold PBS were added into the wells of a DNA high binding plate for further ELISA determination. The amount of CPD in each sample was determined by comparing its absorbance with the absorbance of a known CPD-DNA standard curve.

7. Measurement of IL-6 and IL-8 Expression

Figure 6:
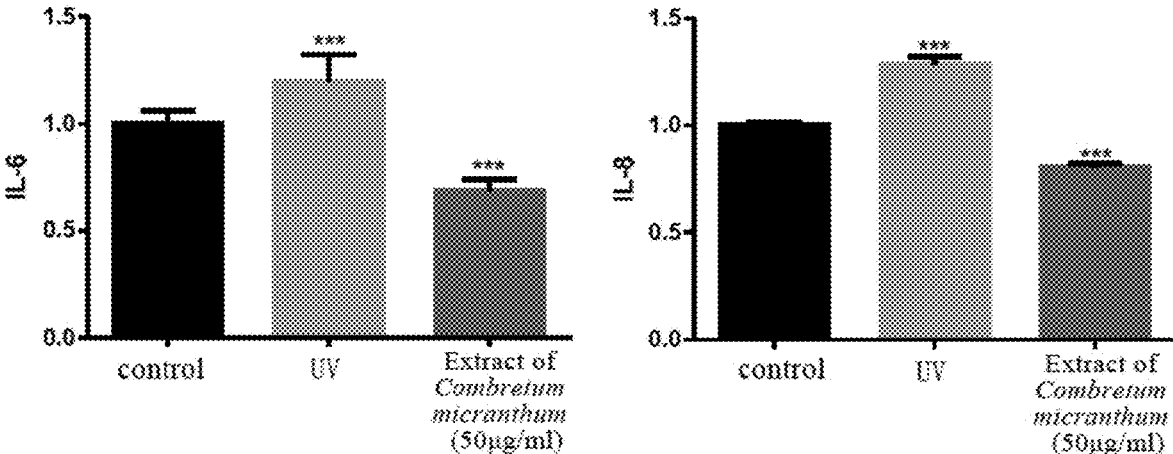
FIG. 6 shows that the water extract of *Combretum micranthum* reduces production of IL-6 and IL-8 under UV conditions.

Human IL-6 ELISA Kit (ab178013) and Human IL-8 ELISA Kit (ab214030) were used. 24 hours before use, keratinocytes at a density of $2\times10^5$/well were seeded in a 24-well plate with or without treatment with the water extract of *Combretum micranthum*. Subsequent measurements was conducted according to the manufacturer's instructions. The results are shown in FIG. 6. The results showed that *Combretum micranthum* could significantly inhibit the production of IL-6 and IL-8 induced by ultraviolet, indicating that *Combretum micranthum* had a significant anti-inflammatory effect and could soothe the skin.

8. Clinical Testing 30 volunteers were selected as subjects by dermatologist. 18 subjects finally completed the test, and 12 subjects withdrew due to personal reasons. One day in advance, a uniform skin area of about 5 cm×6 cm was selected on the skin on the front side of the thigh of the subject, and six irradiation holes were set, and the radiation dose of each irradiation hole was increased by a pace of 25%. After 24 hours, the results was observed, the ultraviolet radiation dose required for the earliest appearance of complete and slight erythema was determined as MED. On the test day, an area with a uniform skin tone of about 5 cm×6 cm was selected as the UV-induced erythema area on the other side of the subject's thigh, and the irradiation doses of the 6 irradiation holes were all set to 1.5 MED. Then 6 erythema with uniform color were obtained as the experimental target sites. According to the random table, one irradiated hole was used as a blank control without any application.

The skin color was measured with a spectrophotometer to measure the values of L*, a* and b* The a* value was used to evaluate the redness of the skin, and it was an important indicator reflecting the anti-inflammatory and soothing ability of the product. The lower the a* value, the better the skin repair. The decrease in a* value represented the degree of repair. The a* value was measured on D1 (Day 1) and D3 (Day 3), in the positive control group (Soothing Gel, Sample 1), *Combretum micranthum* extract (applied after dilution, the application amount was about 20 µg extract per irradiation hole (Sample 2)), and the blank group.

First, assuming that there was no difference in the degree of repair between the two groups. In other words, the decline value of the positive control group and the *Combretum micranthum* extract was not significantly greater than that in the blank group. "D3-D1" was used to indicate the declined value of a* value in these three days; "Δa(1-blk)" represented the degree of difference in the degree of repair between the positive control group and the blank group. Similarly, "Δa(2-blk)" represented the degree of the difference in the degree of repair between the *Combretum micranthum* extract group and the blank group. The differences are shown in Table 1 below.

TABLE 1

Comparison of the decrease of a* value between groups

| | Sample 1 | | Sample 2 | | Blank control group |
| Subject | D 3 – D 1 | Δa(2 – blk) | D 3 – D 1 | Δa(2 – blk) | D 3 – D 1 |
|---|---|---|---|---|---|
| 1 | −0.98 | −0.70 | −1.27 | −1.00 | −0.27 |
| 5 | 0.02 | 0.37 | −0.62 | −0.27 | −0.35 |
| 7 | −0.32 | 0.01 | −0.29 | 0.04 | −0.33 |
| 9 | −1.65 | −0.73 | −1.72 | −0.79 | −0.92 |
| 10 | −0.45 | 0.06 | −0.24 | 0.27 | −0.51 |
| 12 | −0.99 | −1.06 | −0.12 | −0.19 | 0.07 |
| 13 | −0.03 | −0.02 | −0.90 | −0.89 | −0.01 |
| 14 | −1.23 | −0.65 | −0.90 | −0.32 | −0.58 |
| 17 | −0.56 | −0.48 | −0.13 | −0.04 | −0.09 |
| 19 | −1.68 | −0.32 | −2.06 | −0.69 | −1.36 |
| 21 | −1.20 | −1.13 | 0.52 | 0.60 | −0.07 |
| 22 | −2.38 | −0.80 | −2.08 | −0.50 | −1.58 |
| 23 | 0.76 | 0.59 | 0.43 | 0.26 | 0.17 |
| 24 | −1.09 | −0.36 | −1.11 | −0.37 | −0.74 |
| 25 | −2.33 | −1.42 | −1.71 | −0.79 | −0.92 |
| 26 | −0.30 | −0.99 | −0.26 | −0.96 | 0.70 |
| 27 | −1.33 | −0.99 | −0.58 | −0.24 | −0.34 |
| 29 | −2.19 | −0.63 | −2.06 | −0.50 | −1.56 |

The 95% confidence interval of Aa (1-blk) and Aa (2-blk) were calculated, as shown in Table 2. According to the assumption, 0 should be within the 95% confidence interval, but this was not the case. This assumption failed, which meant that compared with the blank group, there was a significant difference in the declined value of the sample. Taking into account the mean value (all less than 0), the positive control (sample 1) and *Combretum micranthum* extract (sample 2) had significantly greater declined values than that in the blank group.

TABLE 2

Difference analysis of the decrease of a* value

| sample | Number of subjects | µ* | 95% Confidence interval |
|---|---|---|---|
| 1 | 18 | −0.51 | $-0.79 < \mu < -0.24$ |
| 2 | 18 | −0.36 | $-0.58 < \mu < -0.13$ |

*µ is Mean value

Test samples (positive control (sample 1) and *Combretum micranthum* extract (sample 2)) were applied to the test area of 18 subjects for 2 days. According to the test statistics, it could be seen that compared with the blank group, *Combretum micranthum* extract significantly improved the repair degree of UV-induced erythema (1.5 MED), indicating that *Combretum micranthum* had significant effects of post-sun repair, repair of skin barrier, skin-lightening and anti-freckle.

In summary, the *Combretum micranthum* plant has the effects of moisturizing, anti-inflammatory, post-sun repair, repair of skin barrier, repair of UV-induced DNA damage, skin-lightening, anti-freckle, and anti-glycation. Therefore, it can be added as a new active ingredient in skin care products and medicines.

All the documents cited herein are incorporated into the invention as reference, as if each of them is individually incorporated. Further, it would be appreciated that, in light of the above-described teaching of the invention, the skilled in the art could make various changes or modifications to the invention, and these equivalents are still in the scope of the invention as defined by the appended claims of the application.

The invention claimed is:

1. A method for achieving protection effect on skin of a subject which comprises a step of administering an extract of *Combretum micranthum* plant on the skin of the subject in need of reducing UV-induced keratinocytes damage and increasing the cell viability of the keratinocytes, wherein the protection effect is selected from the group consisting of skin-lightening, anti-freckle, and combination thereof; and the protection effect is achieved by reducing UV-induced keratinocytes damage and increasing the cell viability of the keratinocytes, wherein the extract of *Combretum micranthum* plant is prepared by a method comprising:

using leaves of *Combretum micranthum* plants only as raw material, and a sufficient amount of water is used to extract 1-5 times, thereby obtain an aqueous extract; and removing lipid-soluble components: extracting the aqueous extract with ethyl acetate, so that a residual aqueous solution after extraction with ethyl acetate is the extract of *Combretum micranthum* plant.

2. The method of claim 1, wherein the protection effect is skin-lightening.

3. The method of claim 1, wherein the extract is administered as a pharmaceutical composition or cosmetic composition.

4. The method of claim 3, wherein the formulation of the cosmetic composition is selected from the group consisting of solid formulation, semi-solid formulation, and liquid formulation.

5. The method of claim 3, wherein the formulation of the cosmetic composition is selected from the group consisting of solution, gel, cream, lotion, ointment, cream, paste, cake, powder, and patch.

6. The method of claim 1, wherein the protection effect further comprises post-sun repair.

7. The method of claim 6, wherein the post-sun repair comprises repair ultraviolet-induced acute erythema, repair ultraviolet-induced cell damage, or a combination thereof.

8. The method of claim 1, wherein the extract of *Combretum micranthum* plant is extracted by the method comprises following steps: 500 g of leaves of *Combretum micranthum* were taken, and soaked at 85-100° C. for 30-60 min after enough water was added, adding water and soaking were repeated 1-4 times and the extracts were combined, the extract was concentrated to ⅓-¼ of the original volume, then ethyl acetate was added, then the ethyl acetate phase was removed after extraction, and the aqueous phase was collected, the aqueous phase was concentrated under reduced pressure and lyophilized into powder.

9. An extract of *Combretum micranthum* plant, wherein the extract of *Combretum micranthum* plant is prepared by a method comprising following steps:

using leaves of *Combretum micranthum* plants only as raw material, and a sufficient amount of water is used to extract 1-5 times, thereby obtain an aqueous extract; and a step for removing lipid-soluble components: extracting the aqueous extract with a ethyl acetate, so that the residual aqueous solution after extraction with the ethyl acetate is the extract of *Combretum micranthum* plant wherein the extract of *Combretum micranthum* plant is extracted by the method comprises following steps: 500 g of leaves of *Combretum micranthum* were taken, and soaked at 85-100° C. for 30-60 min after enough water was added, adding water and soaking were repeated 1-4 times and the extracts were combined, the extract was concentrated to ⅓-¼ of the original volume, then ethyl acetate was added, then the ethyl acetate phase was removed after extraction, and the aqueous phase was collected, and the aqueous phase was concentrated under reduced pressure and lyophilized into powder.

*    *    *    *    *